US006518454B1

(12) United States Patent
Arumugam et al.

(10) Patent No.: US 6,518,454 B1
(45) Date of Patent: Feb. 11, 2003

(54) PREPARATION OF ESTERS OF CARBOXYLIC ACIDS

(75) Inventors: Bhaskar Krishna Arumugam, Kingsport, TN (US); Larry Wayne Blair, Gate City, VA (US); Brendan William Boyd, Johnson City, TN (US); Nick Allen Collins, Fall Branch, TN (US); David Anthony Larkin, Johnson City, TN (US); Steven Thomas Perri, Kingsport, TN (US); Chester Wayne Sink, Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

(21) Appl. No.: 09/975,872

(22) Filed: Oct. 12, 2001

(51) Int. Cl.$^7$ .......................... C07C 67/02; C07C 69/66; C07C 59/147; C07C 59/10; C07C 59/08

(52) U.S. Cl. ...................... 560/265; 560/174; 560/185; 562/577; 562/587; 562/589

(58) Field of Search ............................. 560/265, 174, 560/185; 562/577, 587, 589

(56) References Cited

U.S. PATENT DOCUMENTS

| | | |
|---|---|---|
| 2,462,251 A | 2/1949 | Bassford, Jr. et al. |
| 2,491,065 A | 12/1949 | van Eekelen et al. |
| 2,956,070 A | 10/1960 | Jennings et al. |
| 4,182,633 A | 1/1980 | Ishikawa et al. |
| 4,764,276 A | 8/1988 | Berry et al. |
| 4,923,616 A | 5/1990 | Hirata et al. |
| 4,970,002 A | 11/1990 | Ando et al. |
| 5,064,539 A | 11/1991 | Tasimura et al. |
| 5,391,770 A | 2/1995 | Le Fur et al. |
| 5,405,992 A | 4/1995 | Funk et al. |
| 5,744,634 A | * 4/1998 | Veits et al. |
| 5,817,238 A | * 10/1998 | Makino et al. |
| 6,146,534 A | 11/2000 | Grendze et al. |
| 6,153,791 A | 11/2000 | Moore |

FOREIGN PATENT DOCUMENTS

| | | |
|---|---|---|
| DE | 199 38 980.2 A1 | 2/2001 |
| EP | 0 671 405 A1 | 1/1995 |
| WO | WO 99/03853 A1 | 1/1999 |

OTHER PUBLICATIONS

T. Reichstein, A. Grussner, *Helv. Chim. Acta* 17, p. 311, 1934.

Feng and Huang, *Studies of a Membrane Reactor: Esterification Facilitated By Pervaporation*, Chemical Engineering Science, vol. 51, No. 20, pp. 4673–4679, 1996.

Okomoto et al, *Pervaporation–aided Esterification of Oleic Acid*, Journal of Chemical Engineering of Japan, vol. 26, No. 5, pp. 475–481, 1993.

Kwon, et al, *Removal of Water Produced from Lipase–Catalyzed Esterification in Organic Solvent by Pervaporation*, Biotechnology and Bioengineering, vol. 46, pp. 393–395, 1995.

Keurentjes, *The Esterification of Tartaric Acid with Ethanol: Kinetics and Shifting the Equilibrium by Means of Pervaporation*, Chemical Engineering Science, vol. 49, No. 24A, pp. 4681–4689, 1994.

Xiuyuan, et al, *Modified Aromatic Polyimide Membrane Preparation and Pervaporation Results for Esterification System*, Water Treatment, 10, pp. 115–120, 1995.

Kawase et al., *Increased Esterification Conversion by Application Of The Simulated Moving–Bed Reactor*, Chemical Engineering Science, vol. 51, No. 11, pp. 2971–2976, 1996.

Mazzotti et al., *Dynamics Of A Chromatographic Reactor: Esterification Catalyzed By Acidic Resins*, Ind. Eng. Chem. Res. 1997, 36, 3163–3172.

A. Navarro; H. Caruel; L. Rigal; P. Phemius, *Continuous chromatographic separation process: simulated moving bed allowing simultaneous withdrawal of three fractions*, Journal of Chromatography A, 770, pp. 39–50, (1997).

D. B. Broughton, *Production–Scale adsorptive separations of liquid mixtures by simulated moving bed technology*, Separation Science and Technology, 19, 723 (1984–1985).

Wankat, *Rate–Controlled Separations*, Elsevier Applied Science, 1990, p. 524.

\* cited by examiner

*Primary Examiner*—Jafar Parsa
(74) *Attorney, Agent, or Firm*—Cheryl J. Tubach; Bernard J. Graves, Jr.

(57) ABSTRACT

Disclosed is a process wherein a solution of a carboxylic acid in a first solvent and an alcohol are fed to a simulated moving bed reactor (SMBR) containing a solid(s) to produce a first stream comprising a solution of an ester of the carboxylic acid and the alcohol and a second stream comprising the first solvent. The solid(s) present in the SMBR facilitates the esterification reaction and the separation of the first solvent from the carboxylic acid. The process is particularly valuable for the preparation of an alkanol solution of an alkyl 2-keto-L-gulonate ester (AKLG) from an aqueous fermentation broth containing dissolved 2-keto-L-gulonic acid (KLG) by feeding the fermentation broth and an alkanol to a simulated moving bed reactor which contains a solid acidic esterification catalyst to produce a stream comprising an alkanol solution of an ALKG. The alkanol solution of an ALKG may be used directly to convert the ALKG to ascorbic acid (Vitamin C).

14 Claims, 9 Drawing Sheets

PREPARATION OF ESTERS OF CARBOXYLIC ACIDS

FIELD OF THE INVENTION

This invention pertains to a process for the preparation of esters of carboxylic acids. More particularly, the present invention pertains to a process wherein a solution of a carboxylic acid in a first solvent and an alcohol are fed to a simulated moving bed reactor (SMBR) containing a solid(s) to produce a first stream comprising a solution of an ester of the carboxylic acid and the alcohol and a second stream comprising the first solvent contained in the alcohol. The solid(s) present in the SMBR facilitates the esterification reaction and the separation of the first solvent from the carboxylic acid.

BACKGROUND

Due to their importance as commercial products, numerous esters of carboxylic acids are produced on a large scale in the chemical industry. The reaction of an alcohol and a carboxylic acid to form an ester is accompanied by the formation of a molecule of water. Since esterification reactions are generally reversible reactions under conditions of acid catalysis, the water molecule produced by esterification and the ester reverse react to form the alcohol and the carboxylic acid, thus limiting the equilibrium conversion of the carboxylic acid. If any water is present along with the carboxylic acid, it will further limit the extent of esterification. Homogenous acid catalysts frequently are used to catalyze the esterification. The removal of the acid catalyst at the end of the reaction requires additional processing steps.

The esterification of 2-keto-L-gulonic acid (KLG) in the overall process of manufacturing ascorbic acid is an example of an important commercial esterification process. Known commercial processes for the production of ascorbic acid comprise four major sections: (1) a fermentation section wherein a sugar such as glucose or sorbose is subjected to fermentation to produce 2-keto-L-gulonic acid (KLG); (2) the purification and isolation of anhydrous KLG; (3) the conversion of the isolated KLG to an alkyl KLG ester (AKLG) by esterification with an alcohol, typically methanol, and (4) cyclization of the AKLG using stoichiometric amounts of a base to produce L-ascorbic acid. This process has evolved from the original Reichstein Process (T. Reichstein, A. Grussner, Helv. Chim. Acta 17, p. 311, 1934). In traditional processes employed for the production of ascorbic acid from fermentation-derived KLG, the KLG is isolated as a solid from the aqueous fermentation broth by crystallization and drying. Since esterification reactions are equilibrium limited, the isolated KLG normally must be free of water to obtain an acceptable yield of the ester of KLG in the subsequent esterification step. Evaporation of water to obtain dry KLG requires substantial energy and the equipment required to evaporate the water increases the capital cost.

If KLG monohydrate is utilized instead of anhydrous KLG, additional steps to remove the water of hydration are required during the esterification, such as described in Published PCT Patent Application WO 99/03853. Furthermore, during crystallization of KLG, a significant amount of KLG present in the mother liquor stream may not be recovered. Apart from any water that is present in the KLG solids utilized to make the ester, water formed during the esterification reaction limits the equilibrium conversion. Any unreacted KLG results in lost yield. If a homogenous acid catalyst, such as sulfuric acid or hydrochloric acid, is used to catalyze the esterification of KLG ester, removal of the acidic catalysts or salts thereof becomes necessary. Thus, the processes presently employed in the manufacture of ascorbic acid have a number of disadvantages such as (1) high energy requirement and high capital and operating costs occasioned by the isolation of dry KLG, (2) yield loss during the purification of KLG, (3) incomplete conversion of KLG to its ester in the presence of water which is formed during esterification and/or present in the KLG as a result of the KLG manufacturing process, and (4) removal of the homogenous acid esterification catalyst.

Numerous improvements to the traditional processes for the manufacture of ascorbic acid are described in the literature. To address the energy and capital costs involved in isolating dry KLG solids, a process to exchange solvents by simultaneously removing water and adding methanol is proposed in U.S. Pat. No. 6,146,534. In the solvent exchange process described in the '534 patent, an aqueous stream of a carboxylic acid is fed to a simulated moving bed (SMB) unit packed with a basic resin. An organic solvent such as methanol is used as the separating agent to produce (1) a product stream containing the carboxylic acid in the solvent and substantially free of water and (2) a waste stream containing water in methanol. A similar solvent exchange process for dewatering KLG is disclosed in U.S. Pat. No. 6,153,791. The aqueous KLG feed stream contains a significant amount of sugar, e.g., sorbose, remaining from the fermentation as impurity, which also is removed along with the aqueous waste stream thus purifying the KLG. In both processes, though a substantial amount of water is removed from the aqueous KLG solution, some water is present in the organic solvent stream containing KLG. Since the processes disclosed in both the '534 and '791 patents accomplish separation only, an additional step to esterify KLG is required. During the esterification step, the residual water from the separation step and the water formed during the reaction limit the equilibrium conversion of KLG to its ester. The removal of the homogenous acid catalyst used for the esterification is still required.

The extent of esterification can be increased by simultaneously removing water or the ester as the reaction proceeds. WO 9903853 discloses that the esterification of KLG may be carried out in a 2-stage process in which the reaction can be driven to completion by crystallization of methyl 2-keto-L-gulonate coupled with efficient removal of water. This process requires multiple crystallization stages and solid liquid separation equipment. German Patent Application DE 199 38 980 A1 discloses a method for producing $C_1$–$C_{10}$ alkyl KLG esters by the esterification of KLG with a $C_1$–$C_{10}$ alcohol in the presence of an acid catalyst, wherein the esterification is carried out in a liquid film on a hot surface with simultaneous removal of water. This process is simple to operate but requires significant energy and large volumes of alcohol solvent to act as a carrier for water removal. This process does not provide a means to remove impurities. Other known means to enhance the extent of esterification include membrane reactors for the selective removal of water during esterifications described, for example, by Feng and Huang, Studies of a Membrane Reactor: Esterification Facilitated By Pervaporation, Chemical Engineering Science, Vol. 51, No. 20, pp. 4673–4679, 1996; Jennings et al U.S. Pat. No. 2,956,070; Okomoto et al, Pervaporation-aided Esterification of Oleic Acid, Journal of Chemical Engineering of Japan, Vol. 26, No 5, pages 475–481,1993; Kwon, et al, Removal of Water Produced from Lipase- Catalyzed Esterification in Organic Solvent by Pervaporation, Biotechnology and Bioengineering, Vol. 46, pp. 393–395, 1995; Keurentjes, The Esterification of Tartaric Acid with Ethanol: Kinetics and Shifting the Equilibrium by Means of Pervaporation, "Chemical Engineering Science, Vol. 49, No. 24A, pages 4681–4689,1994; and Xiuyuam, et al, Modified Aromatic Polyimide Membrane Preparation and Pervaporation Results for Esterification System," Water Treatment, 10, pages 115–120, 1995. Simulated Moving Bed Reactors have been proposed as another alternative to enhance the extent of esterifications. See, for example, Kawase et al., Increased Esterification Conversion By Application Of The Simulated Moving-Bed Reactor, Chemical Engineering Science, Vol. 51, No 11, pages 2971–2976, 1996; Mazzotti et al., Dynamics Of A Chromatographic Reactor: Esterification Catalyzed By Acidic Resins, Ind. Eng. Chem. Res. 1997, 36, 3163–3172; and U.S. Pat. No. 5,405,992. These publications propose processes that remove water formed during esterification of a carboxylic acid. The process provided by the present invention differs from these disclosures in that it accomplishes a solvent exchange while simultaneously removing water formed during esterification.

Esters of KLG may be produced from KLG monohydrate in anhydrous methanol using sulfuric acid or other strong acid catalysts. If homogenous acids are used, the removal of the acid or salts thereof is required. For example, U.S. Pat. No. 5,391,770 describes a series of steps consisting of esterification of KLG with methanol in the presence of a strong soluble acid followed by a cyclization with an inorganic base and protonation with sulfuric acid. This is a lengthy process and requires crystalline KLG monohydrate and nearly anhydrous conditions to effect esterification and cyclization. U.S. Pat. No. 5,744,634 (European Patent Application EP 0 671 405 A) discloses a process for the production of the methyl or ethyl ester of KLG by esterification of KLG with methanol or ethanol in the presence of an ion exchange resin. The esterification process takes place in a tubular reactor containing an ion exchange resin using a residence time of from 10 to 120 minutes. The process disclosed in U.S. Pat. No. 5,744,634 requires the monohydrate or, preferably, the anhydrous form to esterify KLG with methanol or ethanol.

SUMMARY OF THE INVENTION

The present invention provides a means to prepare an ester of a carboxylic acid utilizing an alcohol and a solution of a carboxylic acid in a first solvent wherein (1) the first solvent present in the carboxylic acid feed is removed, (2) some or all of any impurities present in the carboxylic acid feed may be removed, (3) the conversion of the carboxylic acid to its ester is enhanced by simultaneously removing water, and (4) the need to use, remove, and dispose of a homogenous acid catalyst normally used to esterify the carboxylic acid is eliminated. The present invention provides a process for the preparation of a solution of a carboxylic acid ester which comprises the steps of:

I. feeding (i) a carboxylic acid in the form of a solution comprising the carboxylic acid and a first solvent; (ii) an alcohol; and (iii) a second solvent which is miscible with the first solvent, to a simulated moving bed reactor containing a solid that is water and alcohol insoluble, catalyzes the esterification of the carboxylic acid, and has different affinities for the carboxylic acid and the first solvent; wherein the carboxylic acid and alcohol react to form a carboxylic acid ester; and II. removing from the simulated moving bed reactor (i) a first liquid stream comprising a solution of the carboxylic acid ester in the second solvent and (ii) a second liquid stream comprising the first solvent and water formed during esterification of the carboxylic acid.

A preferred embodiment of the present invention is represented by a process for the preparation of an alkanol solution of an alkyl 2-keto-L-gulonate ester by the steps comprising:

I. feeding (i) an aqueous solution of 2-keto-L-gulonic acid (KLG) and (ii) an alkanol to a simulated moving bed reactor containing a strong acid cation exchange resin that is water and alcohol insoluble, catalyzes the esterification of the carboxylic acid, and has different affinities for KLG and water, wherein the KLG and alkanol react to form an alkyl 2-keto-L-gulonate ester (AKLG); and II. removing from the simulated moving bed reactor (i) a first liquid stream comprising a solution of the AKLG in the alkanol and (ii) a second liquid stream comprising water derived from the aqueous solution of KLG of step I. and water formed during the reaction of the KLG and alkanol.

Our novel process yields greater than equilibrium conversions of carboxylic acids to carboxylic acid esters such as alkyl carboxylates by separating the carboxylic acid ester from water. In accordance with the above-described preferred embodiment of our novel process, the ester of 2-keto-L-gulonic acid is removed as a solution in the alkanol and may be converted to ascorbic by acid cyclization or a variation of the Reichstein process. Water that is formed during esterification and that is present in the KLG feed, e.g., a KLG-containing fermentation broth, is removed as a waste stream from the simulated moving bed reactor. Some impurities which may be present in KLG-containing fermentation broths may be removed in the aqueous waste stream. The alkanol present in the waste stream can be recovered by various methods such as distillation.

BRIEF DESCRIPTION OF THE DRAWINGS

Accompanying

DETAILED DESCRIPTION OF INVENTION

The process provided by the present invention may be employed to produce a variety of carboxylic acid esters from various carboxylic acids and alcohols. Examples of carboxylic acids which may be used include carboxylic acids containing up to about 10 carbon atoms, preferably aliphatic, carboxylic acids containing 2 to 8 carbon atoms. Specific examples of suitable carboxylic acids include acetic, propionic, furoic, lactic, gluconic, gulonic, oxallic, 2-keto-D-gluconic and KLG. The alcohols which may be used in the process may contain up to about 8 carbon atoms and typically are unsubstituted or substituted aliphatic alcohols. Ethanol and methanol represent the most preferred alcohol reactants and solvents.

The process of our invention is described and illustrated herein with particular reference to the esterification of KLG in the form of a fermentation broth containing KLG to form a KLG ester, specifically methyl 2-keto-L-gulonate (MeKLG). In the first of our novel process, a fermentation broth comprising an aqueous solution of KLG is fed to a simulated moving bed reactor. The fermentation broth typically is produced by the cultivation of one or more microorganisms to produce KLG and/or a precursor thereof. In addition to KLG and water, these fermentation broths typically contain other dissolved materials such as the nutrients required by the microorganism(s) being employed to produce KLG including, for example, amino acids, inorganic and/or organic salts, carbohydrates such as glucose, sorbose, mannose, disaccharides, and trisaccharides, depending upon the sugar feedstock to the fermenter, and various growth factors. The fermentation broth normally is filtered to remove biomass and other insoluble materials and may be treated with activated charcoal for color removal prior to being used in our novel esterification/solvent exchange/purification process.

Figure 2:
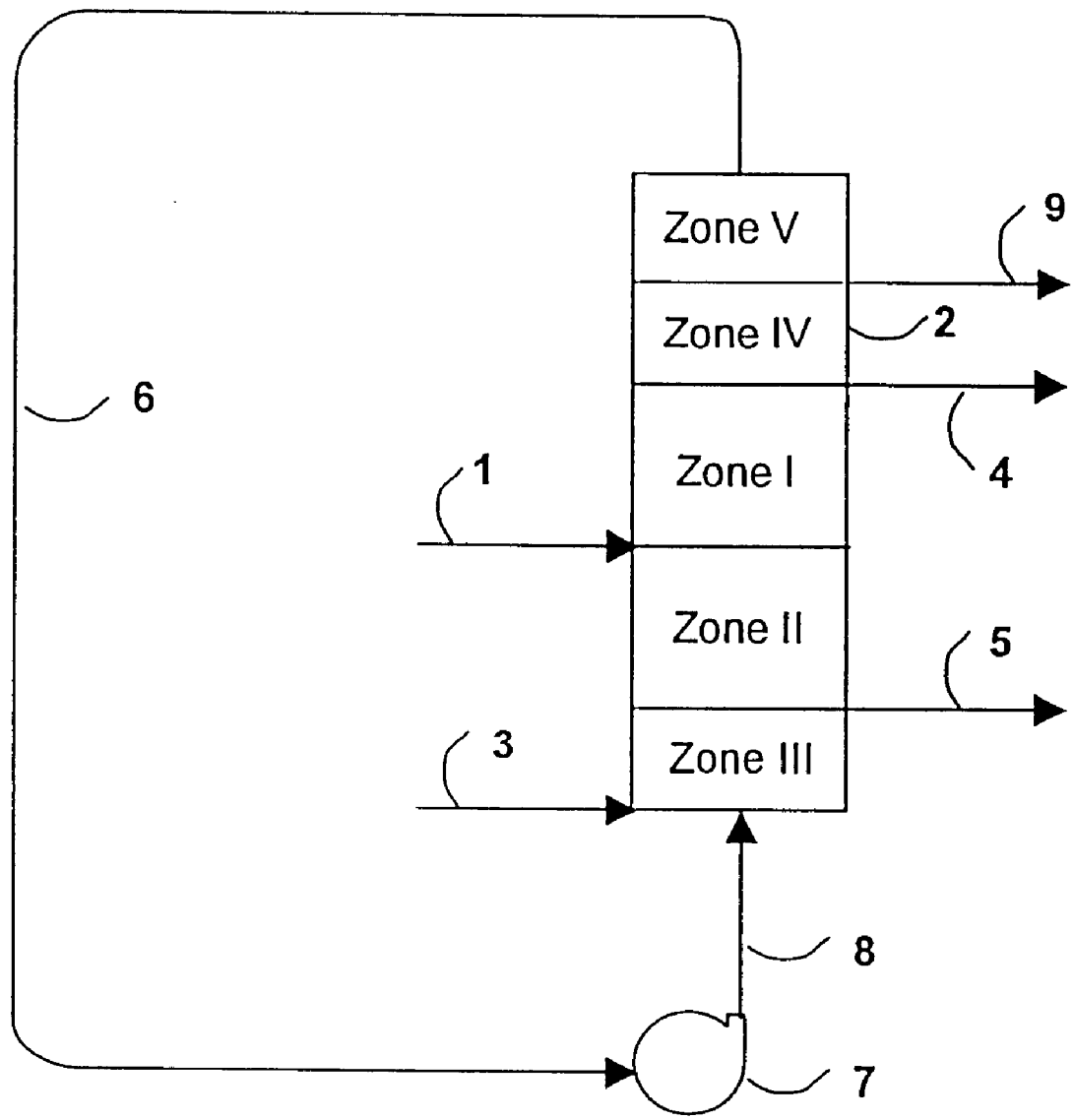

Esterification/solvent exchange/purification of KLG according to the present invention is improved when the KLG present is in the form of the free acid, rather than as a salt. If large amounts of cations such as calcium ions are present, the effectiveness of the esterification catalyst may be diminished. Thus, it is preferred that cations such as calcium, sodium, magnesium, and potassium ions are removed if they should be present in the aqueous KLG feed solution. Such cations may be removed according to conventional procedures such as, for example, precipitation using sulfuric acid and using strongly acidic cation exchange resins. Anions such as sulfates, phosphates, and chlorides may be removed from the aqueous feed although it is not necessary. The anions and cations also may be removed by alternate processes such as electrodialysis. The aqueous KLG stream may be preconcentrated prior to being fed to the simulated moving bed reactor. If anions are not removed from the aqueous KLG feed solution, some of the anions may be removed in the SMB reactor along with water which is withdrawn as the second liquid stream. Alternatively, anions may be removed as a separate third stream using a modified SMB operation such as the procedures described in U.S. Pat. No. 4,970,002 and by A. Navarro; H. Caruel; L. Rigal; P. Phemius, Continuous chromatographic separation process: simulated moving bed allowing simultaneous withdrawal of three fractions, Journal of Chromatography A, 770, pages 39–50, (1997). FIG. 2 shows a schematic representation of one implementation of a SMB to withdraw three products. The operation is similar to the operation of a typical four zone SMB except that a third stream (Stream 9 in FIG. 2) is withdrawn from the SMB reactor. This third stream will contain impurities such as organic and inorganic acids (or their esters) that are stronger than KLG since they will be excluded more than KLG and will travel faster than KLG through the column.

The fermentation broth comprising an aqueous solution of KLG is fed to the simulated moving bed reactor in accordance with the present invention typically comprises about 0.5 to 50 weight percent, more typically about 7 to 15 weight percent, KLG; and about 50 to 98 weight percent, more typically about 75 to 95 weight percent, water. The weight ratio of dissolved KLG to dissolved impurities may be in the range of about 2:1 to 10:1.

Figure 1:
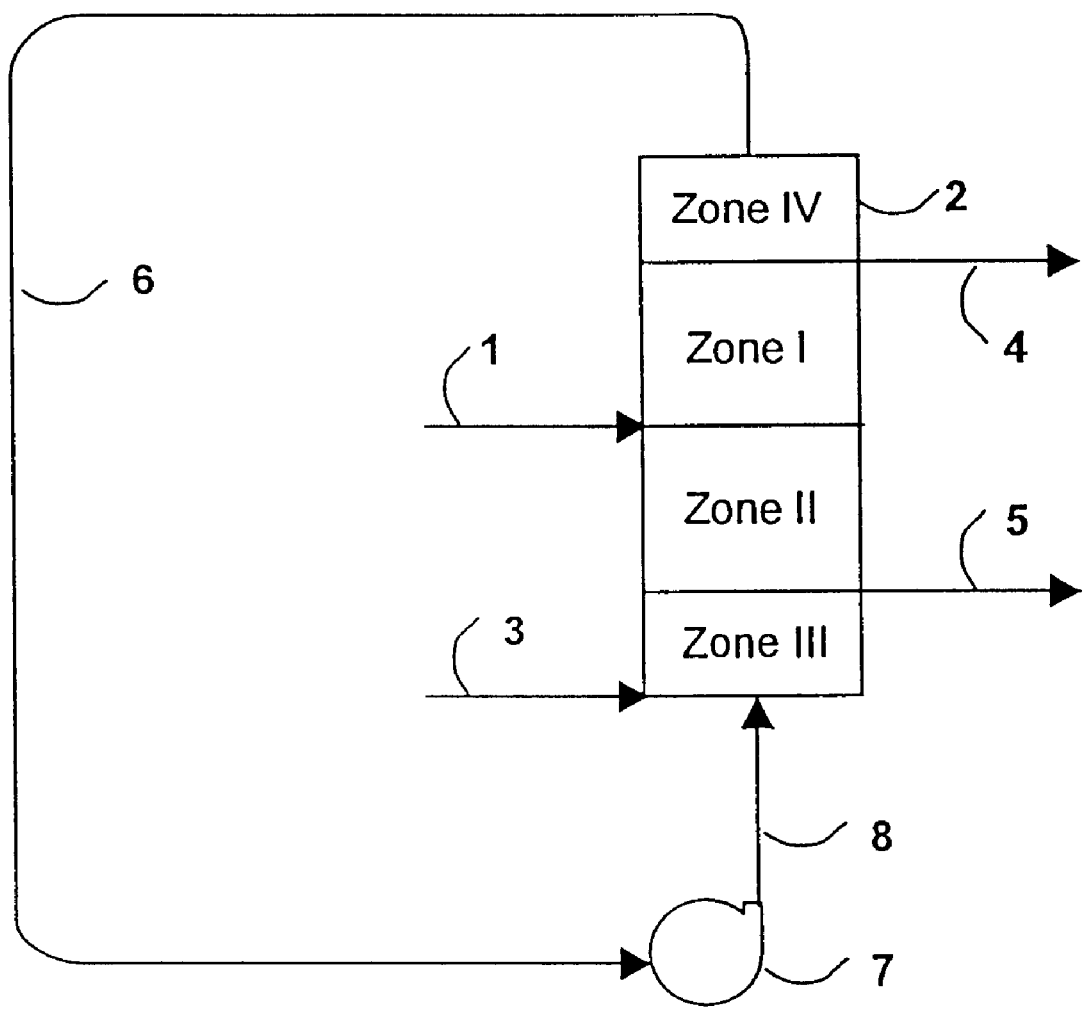
FIG. 1, 2 and 3 are schematic and process flow diagrams illustrating simple simulated moving bed reactor systems embodying the principles of the present invention for producing an alkanol solution of a KLG ester according to a preferred embodiment of the invention.

The simulated moving bed (SMB) reactor utilized in the present invention is a known apparatus and comprises one or more chambers or columns, each of which contains a solid esterification catalyst. As depicted in FIG. 1, the SMB reactor 1 may consist of a single chamber or column comprising a plurality of sections or zones depicted in FIG. 1 as zone I, II, III and IV. The SMB reactor is packed with a strong acidic cation exchange resin and typically is equipped with a plurality of inlet and outlet ports. For example, the reactor may be equipped with two inlet streams, one a feed stream containing the carboxylic acid dissolved in the first solvent and the second a feed stream for the displacer or desorbent. The displacer or desorbent may be, and preferably is, the alcohol reactant for the conversion of the carboxylic acid to a carboxylate ester. The reactor is equipped with a rotary valve or a plurality of valves arranged in a manner such that any feed stream may be introduced to any section or zone and any outlet or effluent stream may be withdrawn from any section or zone. During the operation of the SMB unit, the sections to which the feed streams are fed and from which the outlet streams are withdrawn from change. Thus, in the preferred embodiment of the invention, a feed stream comprising an aqueous solution of KLG along with some impurities is fed to a section of the SMB unit. To a different section, the desorbent stream, typically an alcohol, is fed. The alcohol functions, in combination with the solid packing, to separate KLG and water, and to react, catalyzed by the solid esterification catalyst, with KLG to form an ester of KLG. The effluent streams from the SMB unit comprise (1) a first liquid stream comprising a solution of an AKLG ester in the alcohol and (ii) a second liquid stream comprising water, alcohol and usually some impurities, and alcohol. To achieve separation of AKLG from water, the locations of the inlet and outlet streams are moved intermittently in the direction of liquid flow. The intermittent port movement in the direction of liquid flow simulates the counter-current movement of the bed or beds of the solid(s), e.g., the solid esterification catalyst. Different equipment and operational strategies have been used to simulate the counter-current movement of the solid with respect to the liquid. See, for example, D. B. Broughton, Production-Scale adsorptive separations of liquid mixtures by simulated moving bed technology, Separation Science and Technology, 19, 723 (1984–1985) and U.S. Pat. Nos. 4,764,276, 4,923,616, 4,182,633, and 5,064,539. The process of the present invention may be carried out with all such variations of the SMB concept. A detailed description of the basic SMB process is provided by Wankat, Rate-Controlled Separations, Elsevier Applied Science, 1990, page 524 and a description of the SMB reactor concept is provided by Mazzotti et al. (Marco Mazzotti, Bernardo Neri, Davino Gelosa, and Massimo Morbidelli, Dynamics Of A Chromatographic Reactor Esterification Catalyzed By Acidic Resins, Ind. Eng. Chem. Res. 1997, 36,3163–3172).

Figure 3:
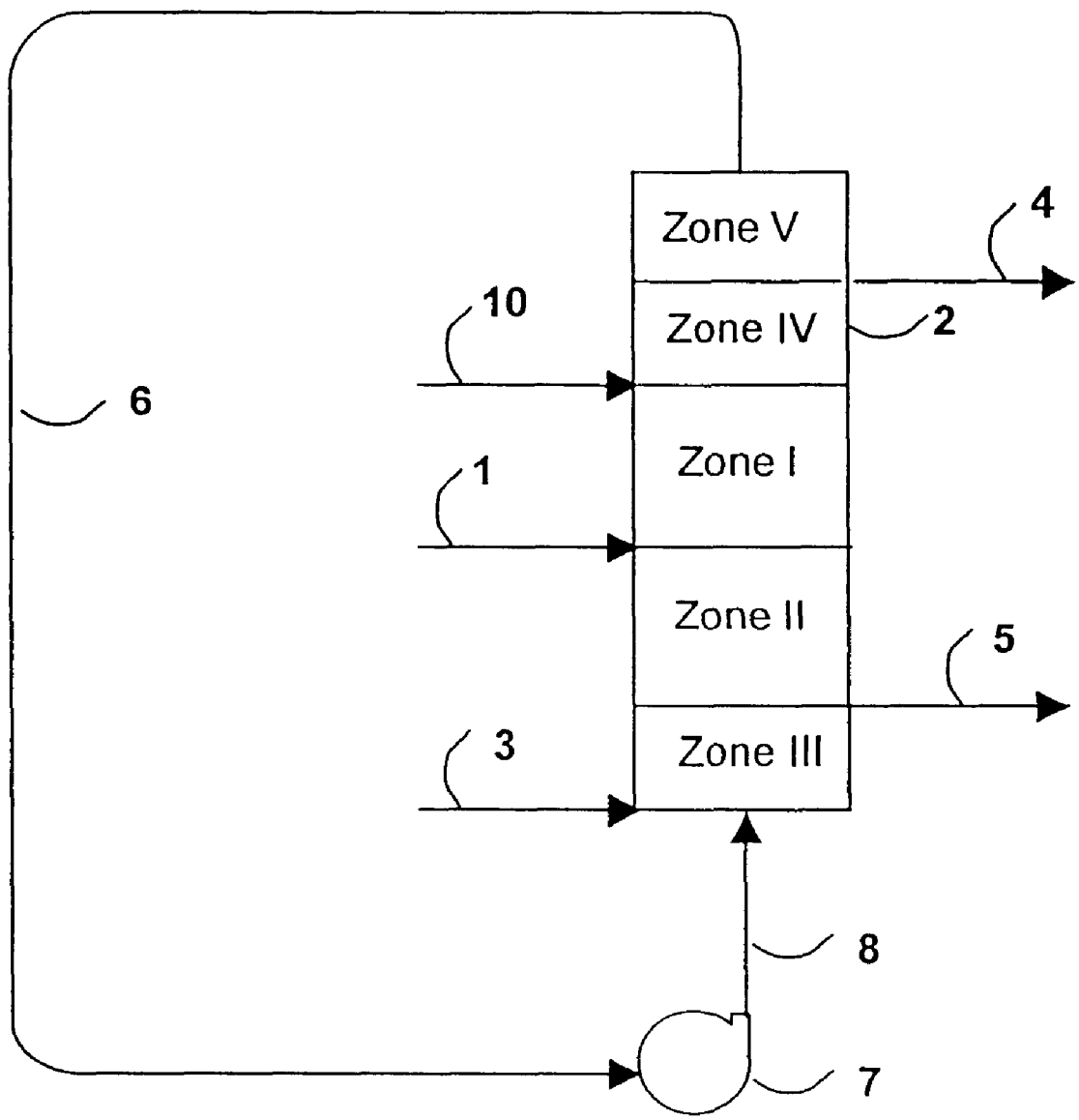

The desorbent may be an alcohol, e.g., a straight- or branched-chain, unsubstituted or substituted alkanol containing up to about 8 carbon atoms, that is miscible with the carboxylic acid feed stream under the operating conditions. Diols such as ethylene glycol also may be used as the desorbent. Desorbents other than alcohols such as nitrites, e.g., aceto-nitrile, and aliphatic and cyclic ethers, e.g., dimethyl ether, tetrahydrofuran, and dioxane may be used. If necessary, miscibility of the desorbent and the carboxylic acid feed stream may be facilitated by varying the temperature and/or using a co-solvent or other additive which may be added to either the carboxylic acid feed stream or the desorbent. Solvent pairs such as ethanol-cyclohexanone and tetrahydrofuran-octane are examples of the use of a co-solvent to make the desorbent miscible. The desorbent solvent preferably is an alkanol such as methanol or ethanol which functions as both the esterification reactant and desorber solvent, i.e., an alkanol such as methanol or ethanol may constitute both alcohol (ii) and second solvent (iii) fed in accordance with the first step of our novel process. However, an inert solvent (non-reactive solvent) may be used as the desorbent, in which case the alcohol necessary to form the carboxylate ester may be fed by mixing it with either the desorbent or the carboxylic acid feed or by feeding the alcohol separately as shown in FIG. 3. The volume ratio of the amount of desorbent, comprising the alcohol, a non-reactive solvent, or a mixture of a non-reactive solvent and an alcohol, i.e., feed components (ii) and (iii), fed to the SMB reactor per volume feed component (i) (carboxylic acid dissolved in a first solvent) fed normally is in the range of about 1:1 to 10:1 with a volume ratio of 2:1 to 4:1 being more preferred..

The simulated moving bed reactor contains a solid, esterification catalyst, i.e., a solid which is substantially insoluble in water, the alcohol reactant, and any optional desorbent, co-solvent or other additive employed. The solid catalyst, usually in the form of small beads or particles, has different affinities for the carboxylic acid fed to the SMB reactor and water. The solid esterification normally is capable of catalyzing the esterification of the carboxylic acid and the separation of the first solvent, e.g., water, that is present in the carboxylic acid feed and water that is formed during esterification of the carboxylic acid. The solid catalyst may be a zeolite or other inorganic, acidic material or, preferably, an acidic ion exchange resin, e.g., a polymeric material derived from styrene or styrene and divinylbenzene containing pendant sulfonic acid groups. Acidic ion exchange resins typically are capable of both catalyzing the esterification and separating water fed to and formed in the SMB reactor. Examples of such acidic ion exchange resins include Amberlyst® 15 marketed by Rohm and Haas Company, Dowex® Monosphere 99 H marketed by Dow Chemical Company, and Lewatit® M Si 00, SP112, K1221, and K2641 marketed by Bayer AG. Such acidic ion exchange resins have an affinity for water. The acid sites of the resin tend to exclude carboxylic acids acid due to charge-charge repulsion. This mechanism is commonly referred to as "ion exclusion". The difference in the affinity of the acidic ion exchange resin for water and for a carboxylic acid such as KLG can be utilized advantageously to effect a separation between water present in the carboxylic acid feed and the carboxylic acid. Any neutral impurities present are not excluded by the acidic ion exchange resin since the neutral impurities are not charged molecules. A preferred embodiment of the process of the present invention takes advantage of the difference between the affinity of the acidic ion exchange resin catalyst for KLG and for neutral impurities (molecules which are not charged) to carryout the partial or complete separation of KLG from neutral impurities, e.g., uncharged sugars.

The acidic catalyst present in the SMB reactor catalyzes the reaction of the alcohol with KLG to form an alkyl 2-keto-L-gulonate ester (AKLG). Water formed during esterification is removed from the reaction region because of the resin's affinity for water. Thus, the reaction can be carried out substantially beyond the equilibrium conversion that would be achieved without the removal of water formed during esterification.

The process provided by the present invention is particularly advantageous when the preferred carboxylic acid KLG feed solution comprises a significant amount of water. However, the process may be employed advantageously even with anhydrous carboxylic acids such as KLG, KLG monohydrate, a concentrated aqueous solution of KLG, or a solution of KLG in a solvent other than water since the process provides a means to remove the water formed during esterification. This water removal assists in driving the esterification to higher than equilibrium conversion.

In a variation of the present invention, the simulated moving bed reactor optionally may be packed with more than one type of material. For example, it is possible to use a solid that is optimized for the separation of water and impurities from KLG in combination with the solid catalyst that is optimized for the esterification of KLG. The simulated moving bed unit may be packed with a uniform mixture of two solid materials or the solid materials may be packed in different segments.

The process of the present invention may be carried out over a broad range of temperature and pressure. The temperature may range from about 0° C. up to the boiling point at the operating pressure of the materials fed to the SMB reactor. The preferred temperature range is about ambient to 80° C. More preferably, the operating temperature is between 30 and 60° C. Pressure is not a critical feature of the process. Thus, pressures between about ambient pressure and 35 bars gauge (508 pounds per square inch—psig) may be used. The preferred pressure range is between about 3.5 and 20 bars gauge (51–290 psig).

The effluent removed from the SMB reactor comprises a first liquid stream comprising an alcohol solution of a carboxylate ester, e.g., an AKLG, and a second liquid stream comprising the solvent contained in the carboxylic acid feed, water or reaction, and alcohol. In the preferred embodiment of the present invention, the second liquid stream effluent also may comprise neutral or non-polar impurities, e.g., sugars, present in aqueous solution of KLG fed to the SMB reactor. In the preferred embodiment, the composition of the first liquid stream effluent typically comprises about 0.5 to 40 weight percent KLG ester, 0 to 25 weight percent KLG, 0 to 25 weight percent water, about 50 to 99 weight percent of the alcohol, or mixture of alcohol and auxiliary solvent fed to the SMB reactor, and about 0 to 10 weight percent impurities which either originated from the fermentation broth/solution fed to the SMB reactor or formed as a byproduct of the esterification reaction when using methanol as both the esterification reactant and displacer or desorber, the first liquid stream effluent preferably comprises about 0.5 to 40 weight percent methyl KLG, 0 to 25 weight percent KLG, 0 to 25 weight percent water, about 50 to 99 weight percent of methanol and about 0 to 10 weight percent impurities which originated from the fermentation broth/solution fed to the SMB reactor or formed as a byproduct of the esterification reaction.

The second liquid effluent stream comprising about 2 to 85 weight percent water, about 15 to 98 weight percent of the alcohol, or mixture of alcohol and auxiliary solvent fed to the SMB reactor, and about 0 to 30 weight percent impurities which either originated from the fermentation broth/solution fed to the SMB reactor or formed as a byproduct of the esterification reaction. This stream may also contain some KLG and KLG ester.

The solution of KLG ester obtained from the simulated moving bed reactor may be cyclized directly without isolating the ester. For example, the KLG ester may be treated with an equivalent of an alkali metal bicarbonate, carbonate or alkoxide, e.g., sodium bicarbonate, sodium carbonate and sodium methoxide, to induce cyclization. The ascorbate product may then be isolated using conventional procedures. For example, sodium ascorbate may be isolated from the alcohol solution or treated directly by the action of a strong acid such as sulfuric acid to convert the sodium ascorbate to ascorbic acid. When the strong acid is sulfuric acid, the alkali metal salt of sulfuric acid is insoluble and may be separated by filtration prior to the isolation of ascorbic acid. An alcohol, e.g., methanol, solution of ascorbic acid may then be concentrated to isolate crude ascorbic acid. Further removal of soluble residual salts may be carried out by means of ion exchange by dissolving the ascorbic acid in water and then contacting the solution with a cation and anion exchange resins. Examples of cation exchange resins include Ambersep 200H and Amberlite IRN 77. Examples of anion exchange resins include Duolite A561. Decolorization of the ascorbic acid solution can be carried out prior to isolation by crystallization.

Alternatively, sodium ascorbate may be isolated directly from the alcohol, e.g., methanol, solution by crystallization and filtration. The protonation of sodium ascorbate may be carried out by dissolving the sodium ascorbate in water and contacting the solution with a cation exchange resin. Examples of resins suitable for effecting protonation include Ambersep 200H, Amberlite IRN 77, and the like. Further removal of residual inorganic acids or organic acids other than ascorbic may be carried out with anion exchange resins such as Amberlite A38. Decolorization of the ascorbic acid solution can be carried out prior to isolation by crystallization.

The solution of the methyl ester of KLG from the SMB reactor also may be cyclized to ascorbic acid in a solvent using an acid catalyst (U.S. Pat. Nos. 2,491,065 and 2,462,251). The acid catalyst may be a homogenous acid such as sulfuric or hydrochloric acid.

The operation of the SMB reactor is described in detail herein for the esterification of KLG to methyl KLG. The SMB unit normally comprises a plurality of sections or zones, typically 4–12 sections, packed with an acidic, cation exchange resin in hydrogen form. Referring to accompanying FIG. 1, a fermentation broth comprising an aqueous solution containing approximately 10 weight percent KLG is fed via conduit 1 to SMB reactor 2 which typically is a cylindrical vessel filled with an acidic, ion exchange resin such as DOWEX Monosphere 99 H resin. SMB reactor 2 comprises 4 zones: I, II, III and IV as shown in FIG. 1. Methanol which functions as both desorbent and esterification reactant is fed to SMB reactor 2 through conduit 3. A portion of the contents of SMB reactor 2 is removed from the top of the SMB reactor and recycled via line 6, pump 7 and line 8 to the base of the SMB reactor. A first liquid product stream comprising methyl KLG in methanol, typically methanol containing about 5 to 25 weight percent methyl KLG and less than about 2% weight percent water, is removed from SMB reactor 2 via conduit 4. A second stream comprising water typically containing from 25 to 60 weight percent water and up to 5 weight percent impurities contained in the aqueous stream fed via conduit 1 is removed from the SMB reactor from conduit 5. The direction of liquid flow within SMB reactor 2 is set by the recycle pump and the direction of liquid flow is from Zone II to Zone I. The KLG-containing fermentation broth is fed between zones I and II of SMB reactor 2. KLG is excluded from the cation exchange resin by the ion exclusion mechanism. Water present in the feed stream is absorbed preferentially by the resin. The combination of ion exclusion of KLG and absorption of water by the acidic ion exchange resin, results in the resin possessing different affinities for KLG and water. As a result, KLG travels faster than water over and through the resin. By setting appropriate flow conditions in zones I and II and an appropriate step time for switching the locations of inlet and outlet streams, water can be separated from KLG and obtained as a separate stream which is withdrawn from a port located between zones II and III (Stream 4 in FIG. 1). As KLG separates from water, the methyl ester of KLG is formed by the catalytic action of the cation exchange resin. Methyl KLG is withdrawn from a port between zones I and IV (Stream 3 in FIG. 1).

FIG. 2 is a process flow diagram similar to that described above for FIG. 1 comprising 5 zones: I, II, III, IV and V, which provides for the removal of inorganic acid and other impurities via a third effluent stream. The operation of SMB reactor 2 depicted in FIG. 2 is identical to the operation described above for FIG. 1 except that a third stream (conduit 9 in FIG. 2) is withdrawn from SMB reactor 2. This third stream typically contains impurities such as organic and inorganic acids and/or esters thereof that are stronger than KLG since they will be excluded more than KLG and will travel faster than KLG through the column. FIG. 3 is a process flow diagram similar to that described above for FIG. 1 comprising 5 zones: I, II, III, IV and V, which provides for an additional feed of a desorbent. The operation of SMB reactor 2 depicted in FIG. 3 is identical to the operation described above for FIG. 1 except that the alcohol reactant required for the esterification reaction is fed to SMB reactor 2 via conduit 10. A desorbent other than an alcohol, e.g., acetonitrile, is fed to SMB reactor 2 via conduit 3. A first liquid product stream comprising methyl KLG in the desorbent, e.g., acetonitrile containing about 75 to 95 weight percent methyl KLG and less than about 2% weight percent water, is removed from SMB reactor 2 via conduit 4. The embodiment illustrated by FIG. 3 may be modified by premixing the alcohol required for esterification with the feed stream, i.e., with the KLG-containing fermentation broth fed via conduit 1 to SMB reactor 2, or by mixing it with the non-alcohol desorbent, supplied to SMB reactor 2 through conduit 3, or by feeding it as a separate stream as shown in FIG. 3.

EXAMPLES

The process provided by our invention is further illustrated by the following examples. All percentages given in the examples are by weight unless specified otherwise. KLG, KLG esters, and ascorbic acid were analyzed by liquid chromatography and water was analyzed by Karl-Fischer method. Pulse tests were conducted to determine the feasibility of a SMB separation. A column is packed with a solid that is capable of separating the different components in the feed mixture. The column is preconditioned by pumping a mobile phase such as water or methanol. A pulse of the feed mixture is introduced into the column. This is followed by elution of the feed mixture by pumping the mobile phase through the column. Effluent fractions are analyzed and a chromatogram prepared by plotting the concentration of various components in the effluent fractions against the elution time or volume. A peak-to-peak separation between the elution peaks of the components to be separated demonstrates the feasibility of separation of the two components using a SMB or SMB reactor. A SMB or SMB reactor may be designed by those skilled in the art based on information obtained from pulse tests. In the examples presented here, pulse tests were carried using DOWEX Monosphere 99 H resin as the solid that separates KLG and water. The solid also serves as the acidic esterification catalyst. Since the resin is supplied by the manufacturer in its calcium salt form, the resin was converted to its hydrogen form by passing 50 liters of 7% HCl solution over 10 liters of resin and subsequently rinsing the resin with 100 liters of water to remove HCl and calcium chloride. The DOWEX resin was presoaked in water and then packed in a jacketed glass column. The temperature in the column was maintained by circulating oil from an oil bath through the jacketed glass column. The DOWEX resin in the pulse test column was rinsed with methanol until the water level in the effluent from the column was below 1%. Pulse tests described in the examples were conducted either on the same column or on columns prepared in a similar fashion.

Example 1

A fermentation broth containing KLG as its calcium salt was acidified by adding concentrated sulfuric acid to precipitate calcium sulfate. The precipitated calcium sulfate was separated by filtration and the acidified broth was cation exchanged by passing it over Ambersep® 200H resin (Rohm and Haas Company) to reduce the level of cations. The cation-exchanged broth was anion exchanged by passing it over Duolite® A561 resin (Rohm and Haas Company) to remove anions such as sulfates, phosphates, and chlorides. The resulting solution comprised 9.95% KLG, Ca and Mg below 5 ppm, 15 ppm K, 51 ppm Na, less than 10 ppm P, and 22 ppm S.

Figure 4:
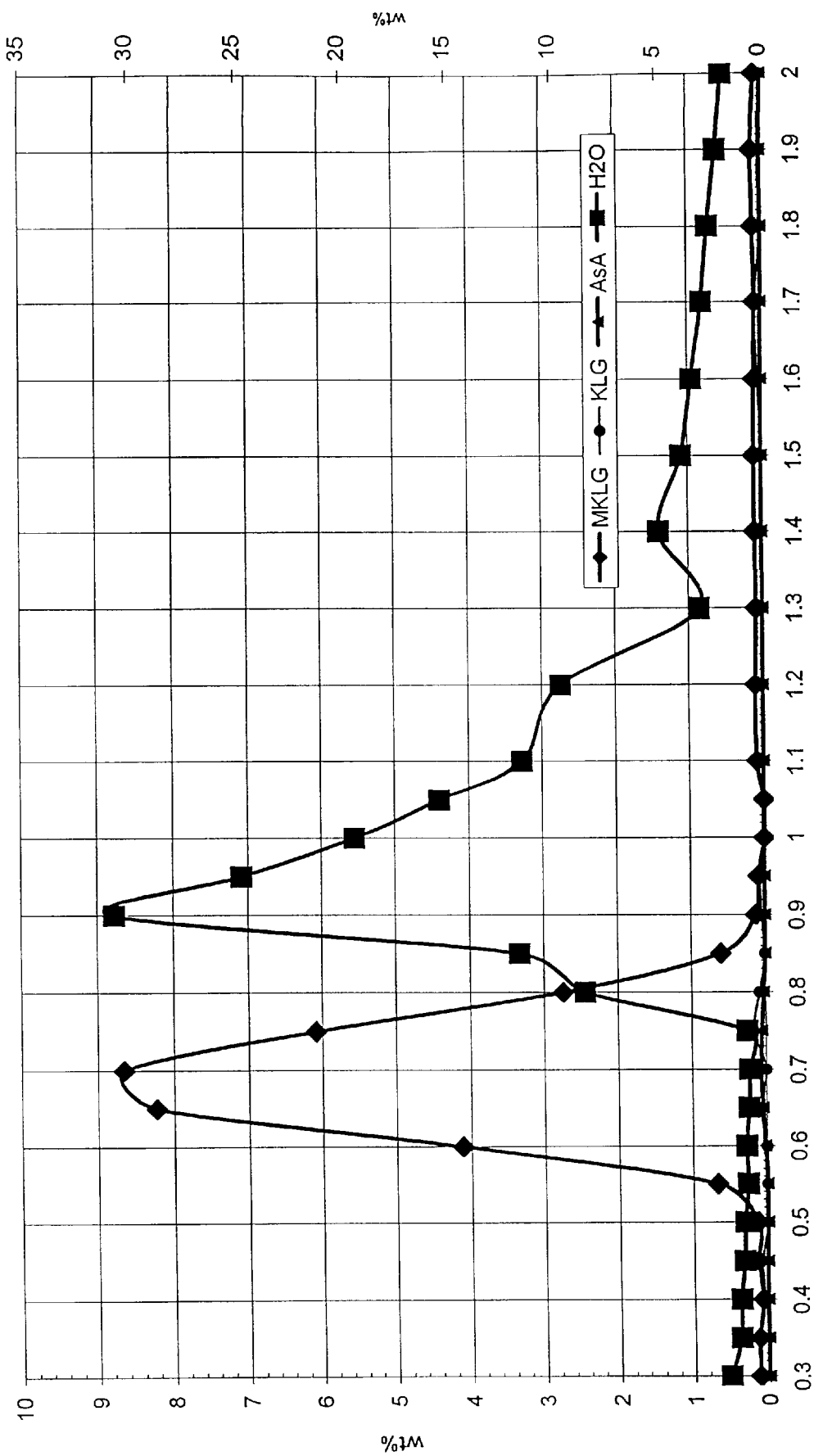
FIGS. 4 to 9 are graphs showing the results of pulse tests conducted with various feed and operating conditions as described in the examples. Each curve of the graphs of FIGS. 4 to 9 refers to the concentration of a component of the product mixtures obtained from the experiments described in the examples. The component referred to by each curve is shown by the legend on each of FIGS. 4 to 9 wherein MKLG and MeKLG refer to methyl 2-keto-L-gulonate, KLG refers to 2-keto-L-gulonic acid, AsA refers to ascorbic acid, H2O refers to water, Ethyl KLG refers to ethyl 2-keto-L-gulonate, P is phosphorus, S is sulfur and Cl is chloride. While the invention is susceptible to embodiment in various forms, there is shown in accompanying FIGS. 1, 2 and 3 and hereinafter described in detail specific embodiments of the invention. The present disclosure is to be considered as an exemplification of the invention without limitation to the specific embodiment illustrated.

A pulse of 53.4 ml of the KLG solution prepared as described in the preceding paragraph was fed at a flow rate of 8.9 ml per minute to the pulse test column (volume=534 ml) described above and maintained at a temperature of 40° C. by a circulating heated oil from a oil bath. The feed to the column was switched back to methanol after completion of the addition of the KLG solution. The effluent from the column was recovered in 26.7 ml fractions. These fractions were analyzed for KLG, MeKLG, and water. The results shown in FIG. 4 establish that most of the KLG was converted to MeKLG and that there is a peak-to-peak separation between MeKLG and water. The horizontal axis is elution time, represented as bed volume. Bed Volume is calculated as:

$$\text{Bed Volumes} = \frac{\text{Volume of effluent collected}}{\text{Volume of column packing}}$$

Concentrations of eluting components is represented along the vertical axis. Since water is adsorbed by the resin, it elutes later than KLG which is excluded by the resin. The amount of KLG in the effluent fractions is negligible since KLG is converted to MeKLG by the catalytic action of the solid. MeKLG elutes considerably earlier than water. There is a significant peak-to-peak separation between MeKLG and water. A peak-to-peak separation between MeKLG and water in a pulse test demonstrates that KLG can be separated from water while simultaneously converting KLG to MeKLG.

Example 2

A fermentation broth containing KLG as its calcium salt was electrodialyzed and anion exchanged to prepare a feed solution comprising 19.93% KLG, 38.5 ppm Ca, 17.2 ppm Na, below detection levels for K and Mg, 116.3 ppm phosphorus, 31.3 ppm sulfur, and 43 ppm chloride. This feed was concentrated on a rotary evaporator under vacuum to obtain a solution that contained 24.4% KLG.

Figure 5:
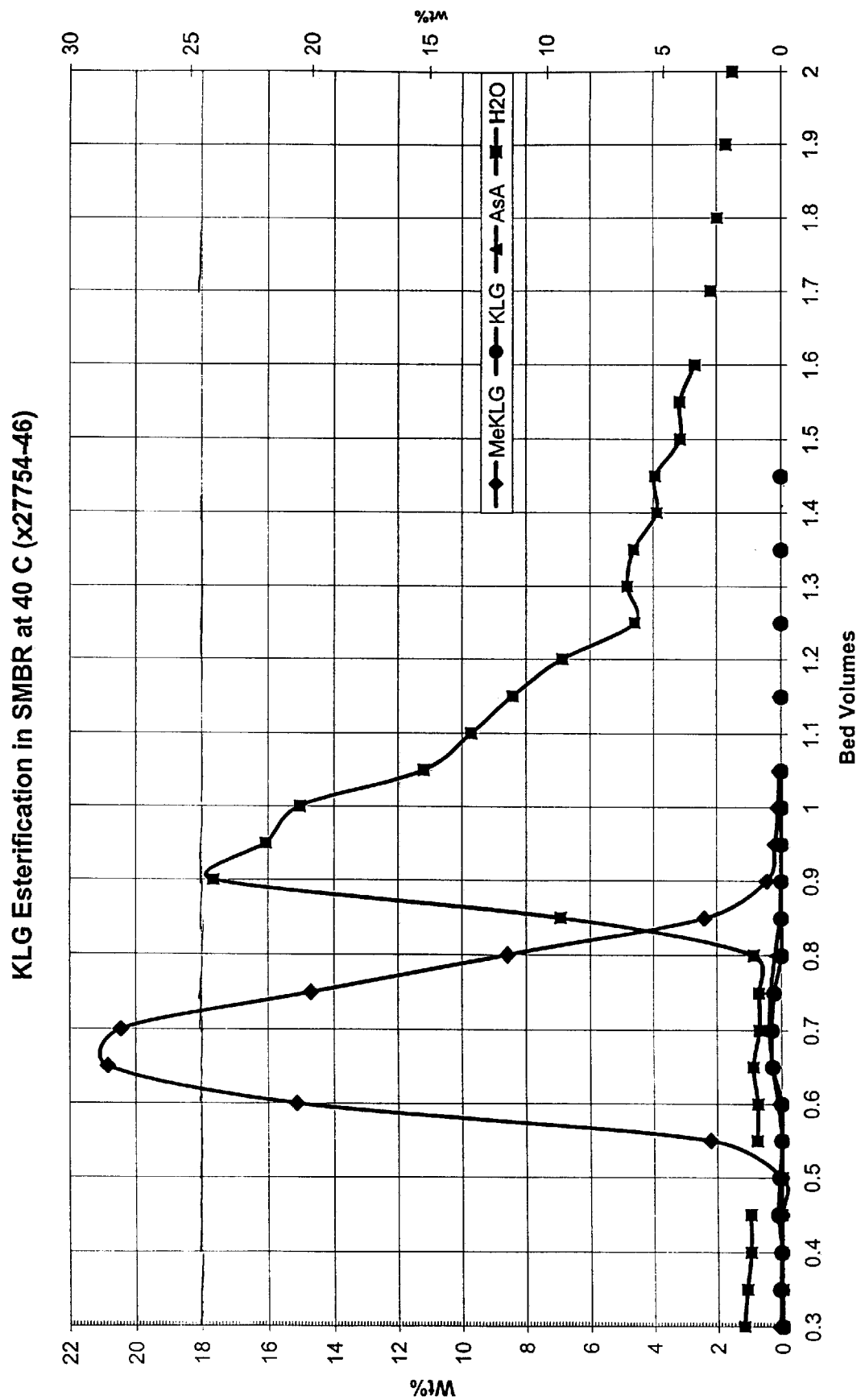

A pulse of 53.4 ml of the KLG solution prepared as described in the preceding paragraph was fed at a flow rate of 8.9 ml/minute to the pulse test column (volume=534 ml) prepared as described above and maintained at 40° C. by circulating heated oil from a oil bath. The feed to the column was switched back to methanol after completion of the addition of the KLG solution. The effluent from the column was recovered in 26.7 ml fractions. These fractions were analyzed for KLG, MeKLG, and water. The results, shown in FIG. 5, establish that most of the KLG was converted to MeKLG and that there is a peak-to-peak separation between MeKLG and water. Since the KLG feed used in this example is more concentrated than that used in Example 1, the concentration of MeKLG in the effluent fractions is, in general, higher. The advantages of using a more concentrated feed include the use of a smaller SMB reactor and less desorbent per unit mass of ester produced.

Example 3

Figure 6:
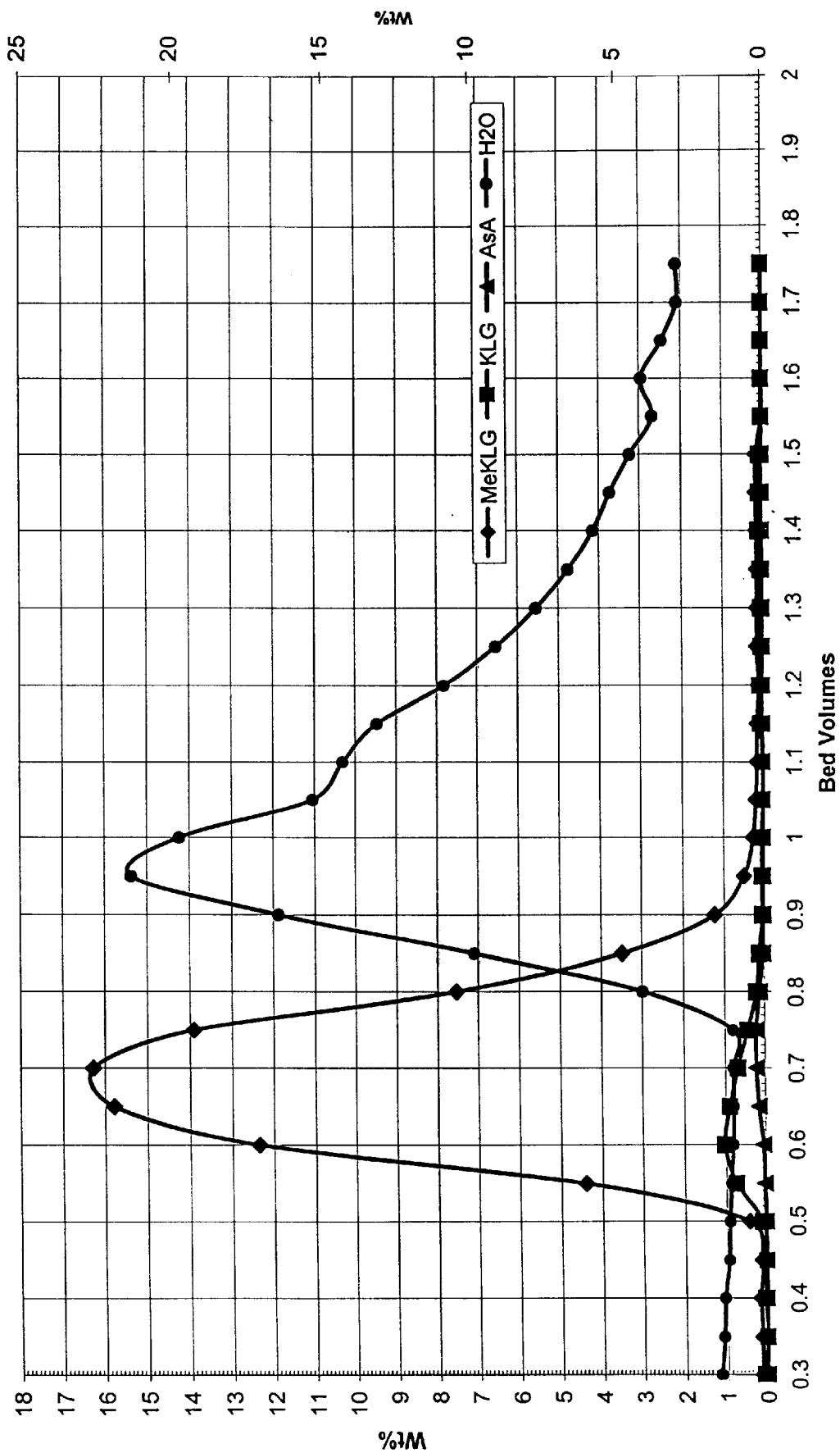

A pulse of 53.4 ml of the KLG solution prepared as described in Example 2 was fed at a flow rate of 8.9 ml/minute to the pulse test column (volume=534 ml) at room temperature prepared as described above and the feed was switched back to methanol. The effluent from the column was recovered in 26.7 ml fractions. These fractions were analyzed for KLG, MeKLG, and water. The results, shown in FIG. 6, establish that most of the KLG was converted to MeKLG though the conversion is slightly lower than that obtained in Example 2 and that there is a peak-to-peak separation between MeKLG and water.

Example 4

Figure 7:
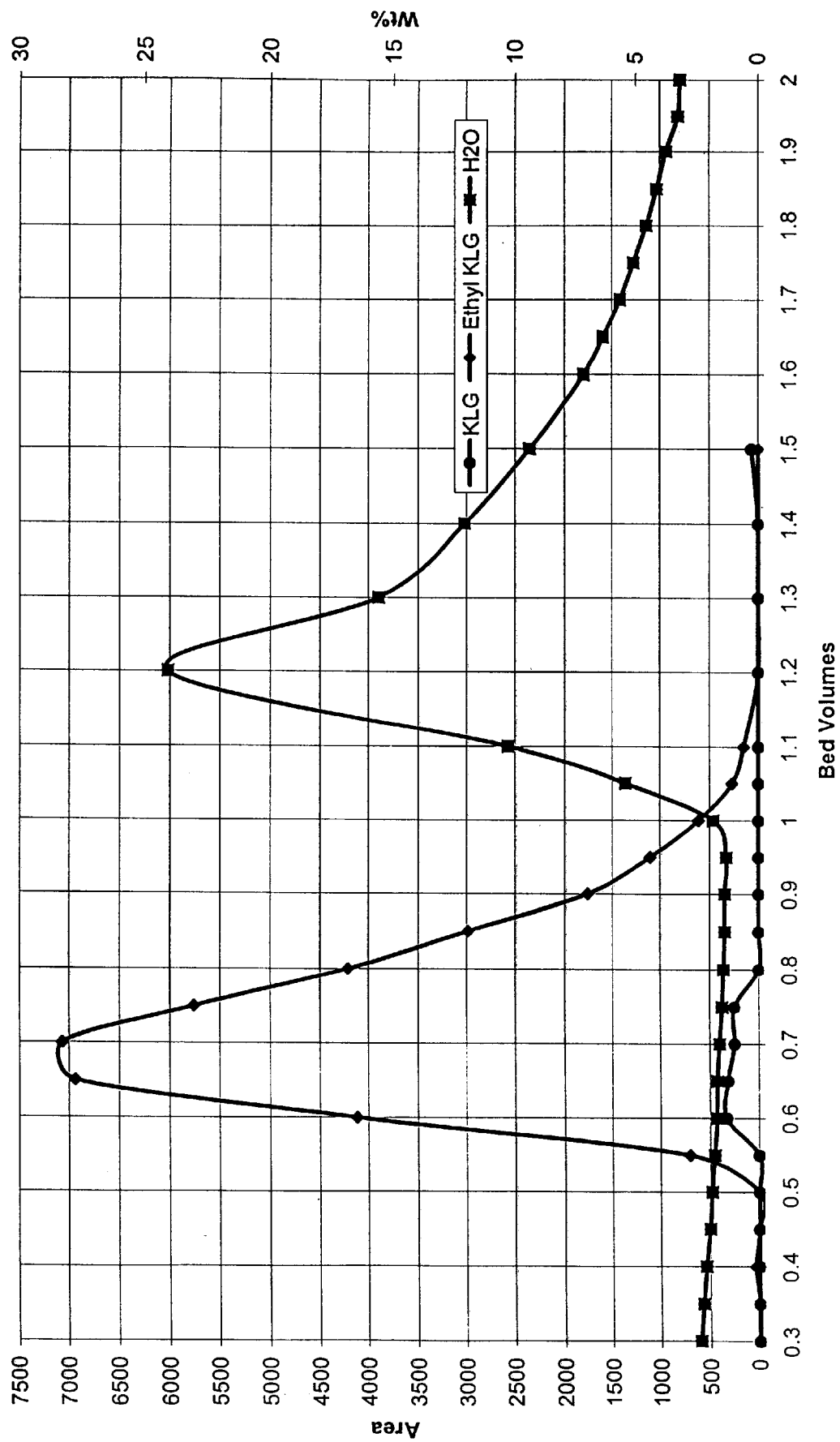

A pulse test column was prepared as described above using 534 ml of DOWEX Monosphere 99 H resin that has been presoaked in water. The temperature in the column was maintained at 45° C. by circulating heated oil from an oil bath. The DOWEX resin in the pulse test column was rinsed with ethanol until the water level in the effluent from the column was below 1%. A pulse of 53.4 ml of the KLG solution prepared as described in Example 1 was fed at a flow rate of 8.9 ml/minute to the pulse test column prepared as described above and maintained at 45° C. The feed to the column was switched back to ethanol after completion of the addition of the KLG solution. The effluent from the column was recovered in 26.7 ml fractions. These fractions were analyzed for KLG, ethyl KLG, and water. In this example, concentrations were reported as peak areas instead of weight percents. The results shown in FIG. 7 establish that most of the KLG was converted to ethyl KLG and that there is a peak-to-peak separation between ethyl KLG and water.

Example 5

Figure 8:
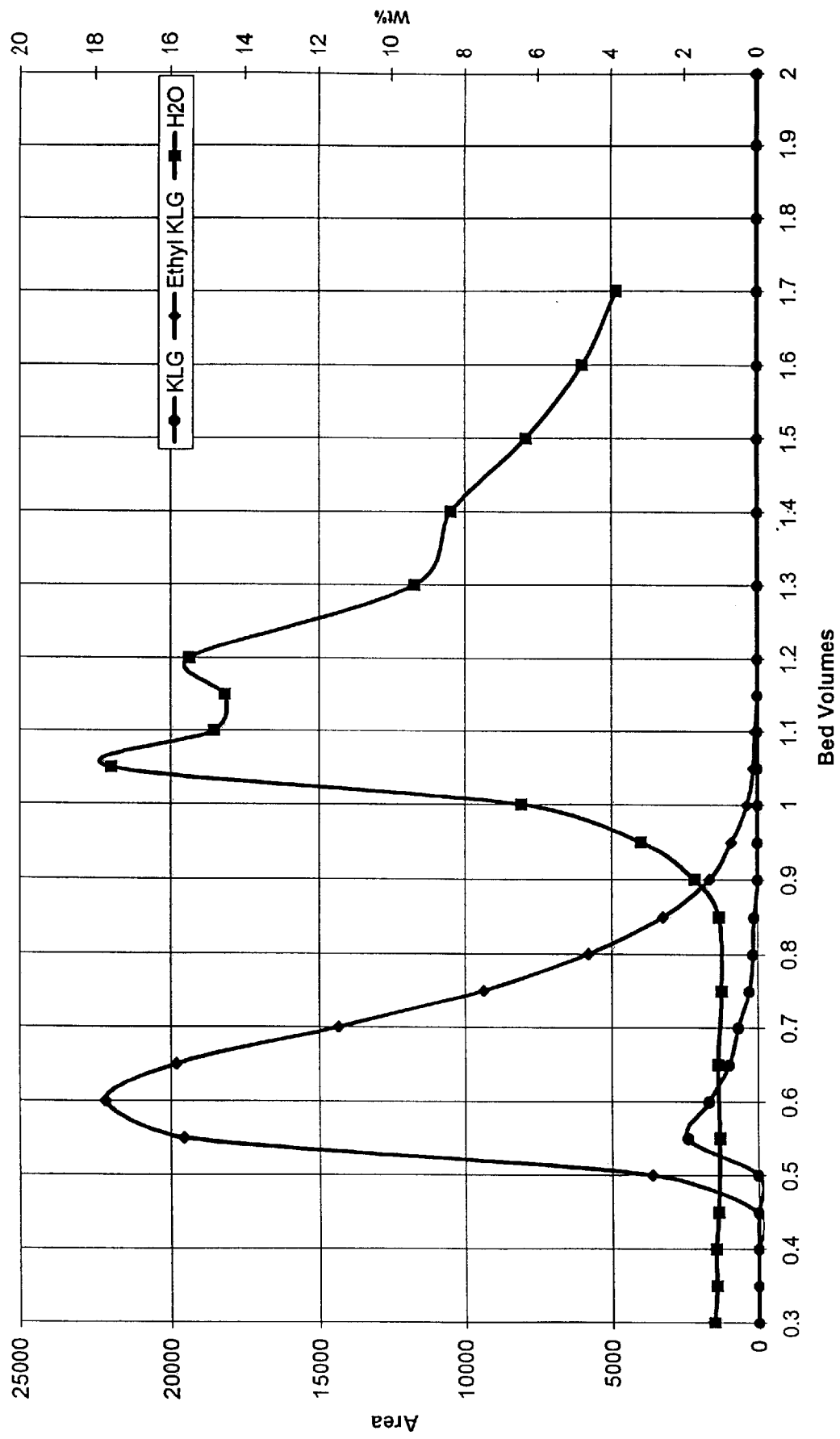

A pulse of 53.4 ml of the KLG solution prepared as described in Example 2 was fed at a flow rate of 8.9 ml/minute to the pulse test column (volume=534 ml) prepared as described in Example 4 above and maintained at 45° C. The feed to the column was switched back to ethanol after completion of the addition of the KLG solution. The effluent from the column was recovered in 26.7 ml fractions. These fractions were analyzed for KLG, ethyl KLG, and water. In this example, concentrations were reported as peak areas instead of weight percents. The results reported in FIG. 8 show that most of the KLG was converted to ethyl KLG and that there is a peak-to-peak separation between ethyl KLG and water.

Example 6

A fermentation broth comprising about 15% 2-keto-L-gulonic acid as its calcium salt was acidified by adding concentrated sulfuric acid to precipitate calcium sulfate. The precipitated calcium sulfate was removed by filtration. Cations such as Ca, Mg, Na, and K were removed from the resulting solution by cation exchange. The resulting solution contained 6 ppm Ca, 3 ppm Mg, 94 ppm Na, 19 ppm K, 3 ppm Fe, less than 3 ppm Ni, 1170 ppm S, 348 ppm P, and 12.65 wt % KLG.

Figure 9:
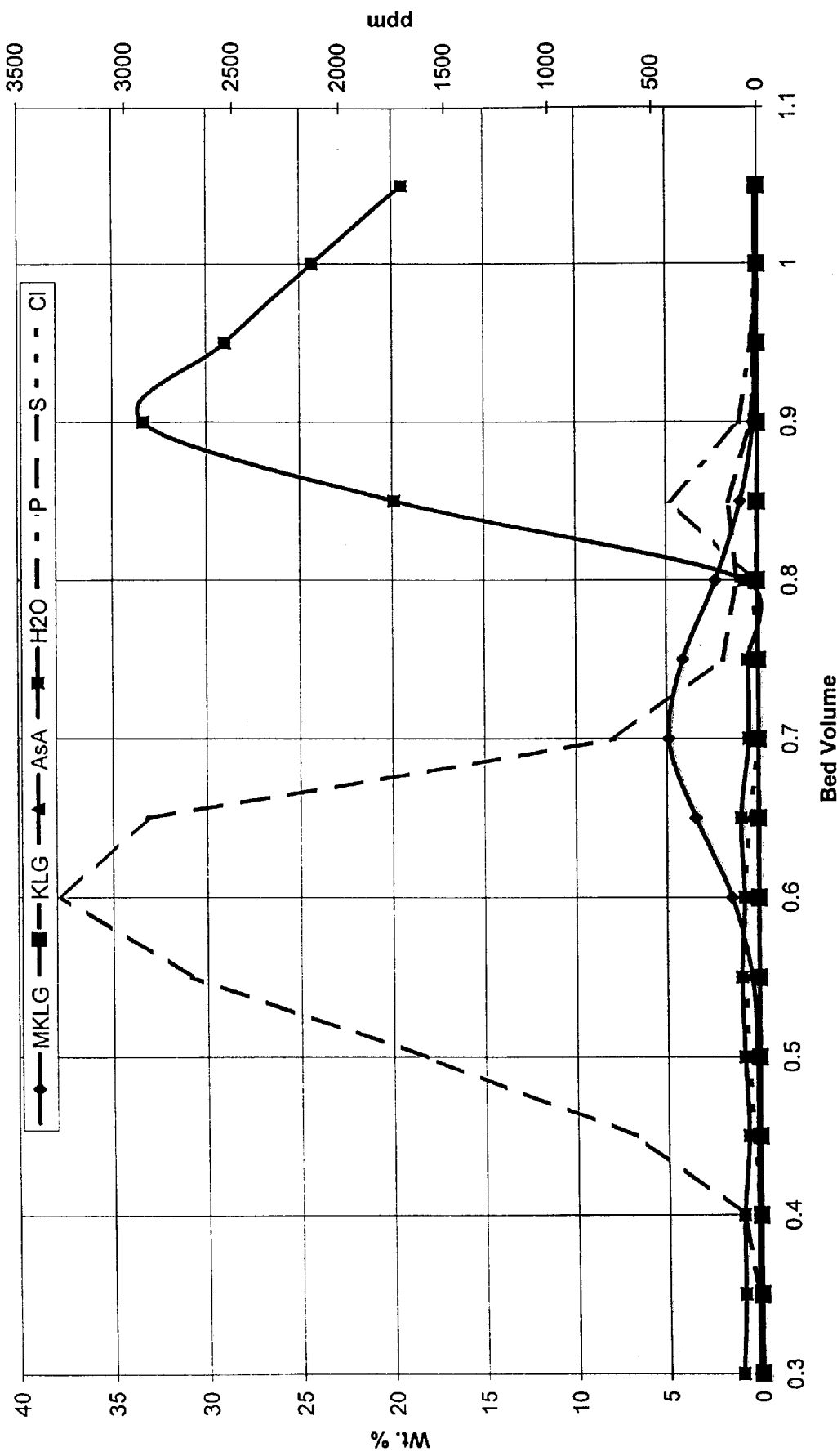

A stainless steel column with a volume of 295 ml was packed with DOWEX Monosphere 99 H resin which had been presoaked in methanol. The resin was rinsed with sufficient methanol to remove most of the water that was present in the resin. A pulse of 29.5 ml of the KLG solution prepared as described in the preceding paragraph was fed at a flow rate of 4.91 ml/minute to the pulse test column prepared as described in herein and maintained at 40° C. by circulating heated oil from an oil bath. The feed to the column was switched back to methanol after completion of the addition of the KLG solution. The effluent from the column was recovered in 14.75 ml fractions. These fractions were analyzed for KLG, MeKLG, and water and anions were measured as elemental sulfur, phosphorus, and chloride. The results reported in FIG. 9 show that most of the KLG was converted to MeKLG and that there is a peak-to-peak separation between MeKLG and water. Sulfur and chlorides elute ahead of MeKLG whereas phosphorus elutes very close to water. With a 5-zone SMB reactor, at least some sulfur and chlorides can be removed. Phosphorus can be removed along with water. Thus, it may be possible to eliminate anion exchange preceding the SMB reactor. Any sulfur and chlorides present in the MeKLG stream may be removed by anion exchange. It also is feasible that sulfur and chlorides will remain in solution as sodium ascorbate precipitates in the base-catalyzed conversion to ascorbic acid.

Example 7

A SMB unit comprising eight columns packed with DOWEX Monosphere 99 H resin was employed in this example of continuous operation of the process of the present invention. The eight identical columns each had a volume of 498 ml. Two columns each were assigned to the between feed and extract, extract and desorbent, desorbent and raffinate, and raffinate and feed. A fermentation broth containing KLG as its calcium salt was acidified by adding concentrated sulfuric acid to precipitate calcium sulfate. The precipitated calcium sulfate was separated by filtration. The acidified broth was cation exchanged to reduce the level of cations. The cation exchanged broth was anion exchanged to remove anions such as sulfates, phosphates, and chlorides. The resulting solution containing 9.26% KLG was fed to the SMB unit at a rate of 8.7 ml/minute from a jacketed container maintained at 55° C. by circulating heated oil from an oil bath. The flow rate of the methanol desorbent was set at 30.3 ml/minute from a jacketed container was maintained at 55° C. by circulating heated oil from an oil bath. The eight jacketed columns were heated by circulating heated oil from an oil bath maintained at 55° C. A raffinate stream comprising 7.36% MeKLG, 0.09% KLG, and 0.65% water in methanol was obtained as product. The extract stream obtained contained 0.19% MeKLG, 0.04% water, and 31.74% KLG. Overall conversion of KLG was 98%. Conversion of KLG is defined as follows:

$$\text{KLG Conversion} = 1 - \frac{\text{Total molar flow of KLG in outlet streams}}{\text{Total molar flow of KLG fed to SMB reactor}}$$

Selectivity of the conversion of KLG to MeKLG was about 100%. Selectivity in this context is defined as:

$$\text{MeKLG Selectivity} = \frac{\text{Total molar flow of MeKLG in outlet streams}}{\text{Total molar flow of KLG fed to SMB reactor}}$$

Since some KLG is lost in the extract stream, the overall yield of MeKLG from KLG was 93%. MeKLG yield is defined as:

$$\text{MeKLG Yield} = \frac{\text{Total molar flow of MeKLG in raffinate stream}}{\text{Total molar flow of KLG fed to SMB reactor}}$$

The invention has been described in detail with particular reference to preferred embodiments thereof, but it will be understood that variations and modifications can be effected within the spirit and scope of the invention.

We claim:

1. A process for the preparation of a solution of an ester of a carboxylic acid which comprises the steps of:
   I. feeding (i) a carboxylic acid in the form of a solution comprising the carboxylic acid and water; (ii) an alcohol; and (iii) a desorbent which is miscible with water, to a simulated moving bed reactor containing a solid that is water and alcohol insoluble, catalyzes the esterification of the carboxylic acid, and has different affinities for the carboxylic acid and water; wherein the carboxylic acid and alcohol react to form a carboxylic acid ester; and
   II. removing from the simulated moving bed reactor (i) a first liquid stream comprising a solution of the carboxylic acid ester in the desorbent and (ii) a second liquid stream comprising water from the carboxylic acid feed from Step I and water formed during esterification of the carboxylic acid.

2. Process according to claim 1 wherein the carboxylic acid contains up to about 10 carbon atoms and the alcohol contains up to about 8 carbon atoms.

3. A process for the preparation of a solution of an ester of a carboxylic acid which comprises the steps of:
   I. feeding (i) an aliphatic carboxylic acid containing 2 to 8 carbon atoms in the form of a solution comprising the carboxylic acid and water; and (ii) an alcohol selected from methanol and ethanol, to a simulated moving bed reactor containing a solid, acidic, ion exchange resin that is water and alcohol insoluble, catalyzes the esterification of the carboxylic acid, and has different affinities for the carboxylic acid and water; wherein the carboxylic acid and alcohol react to form a carboxylic acid ester; and
   II. removing from the simulated moving bed reactor (i) a first liquid stream comprising a solution of the carboxylic acid ester in the alcohol and (ii) a second liquid stream comprising water from the carboxylic acid feed from Step I and water formed during esterification of the carboxylic acid.

4. Process according to claim 3 wherein the simulated moving bed reactor is maintained at a temperature of about 30 to 60° C. and a pressure of about 3.5 to 20 bars gauge.

5. Process according to claim 3 wherein the aliphatic carboxylic acid is lactic acid and the carboxylic acid ester is methyl or ethyl lactate.

6. Process according to claim 5 wherein the simulated moving bed reactor is maintained at a temperature of about 30 to 60° C. and a pressure of about 3.5 to 20 bars gauge.

7. Process according to claim 3 wherein the aliphatic carboxylic acid is 2-keto-D-gluconic acid and the carboxylic acid ester is methyl or ethyl 2-keto-D-gluconate.

8. Process according to claim 7 wherein the simulated moving bed reactor is maintained at a temperature of about 30 to 60° C. and a pressure of about 3.5 to 20 bars gauge.

9. Process for the preparation of an alkanol solution of an alkyl 2-keto-L-gulonate ester by the steps comprising:

I. feeding (i) an aqueous solution of 2-keto-L-gulonic acid (KLG) and (ii) an alkanol to a simulated moving bed reactor containing a strong acid cation exchange resin that is water and alcohol insoluble, catalyzes the esterification of the carboxylic acid, and has different affinities for the carboxylic acid and water, wherein the KLG and alkanol react to form an alkyl 2-keto-L-gulonate ester (AKLG); and II. removing from the simulated moving bed reactor (i) a first liquid stream comprising a solution of the AKLG in the alkanol and (ii) a second liquid stream comprising water derived from the aqueous solution of KLG of step I and water formed during the reaction of the KLG and alkanol.

10. Process according to claim 9 wherein the alkanol is methanol or ethanol and the alkyl 2-keto-L-gulonate ester is methyl or ethyl 2-keto-L-gulonate ester.

11. Process according to claim 9 wherein the alkanol is methanol or ethanol and the simulated moving bed reactor is maintained at a temperature of about 30 to 60° C. and a pressure of about 3.5 to 20 bars gauge.

12. Process according to claim 9 wherein aqueous KLG solution (i) of step I contains about 7 to 15 weight percent KLG and the first liquid stream (i) of step PI comprises 0.5 to 40 weight percent solution of the AKLG in the alkanol.

13. Process according to claim 9 wherein step II. comprises removing from the simulated moving bed reactor (i) a first liquid stream comprising a solution of the AKLG in the alkanol; (ii) a second liquid stream comprising water derived from the aqueous solution of KLG of step I and water formed during the reaction of the KLG and alkanol; and (iii) a third liquid stream comprising an aqueous solution of impurities comprising organic and inorganic acids and/or esters thereof that are stronger than KLG.

14. Process according to claim 9 wherein step I comprises feeding (i) an aqueous solution of KLG; (ii) an alkanol; and (iii) a desorbent other than an alcohol to a simulated moving bed reactor containing a strong acid cation exchange resin that is water and alcohol insoluble, catalyzes the esterification of the carboxylic acid, and has different affinities for the carboxylic acid and water, wherein the KLG and alkanol react to form an AKLG.

* * * * *

UNITED STATES PATENT AND TRADEMARK OFFICE
CERTIFICATE OF CORRECTION

PATENT NO.    : 6,518,454 B1
DATED         : February 11, 2003
INVENTOR(S)   : Arumugam et al.

It is certified that error appears in the above-identified patent and that said Letters Patent is hereby corrected as shown below:

<u>Column 16,</u>
Line 10, "PI" should be -- II --.

Signed and Sealed this

Twenty-second Day of July, 2003

JAMES E. ROGAN
*Director of the United States Patent and Trademark Office*